United States Patent
Gonopolskiy et al.

(10) Patent No.: US 9,404,961 B2
(45) Date of Patent: Aug. 2, 2016

(54) SYSTEM AND METHOD OF DETERMINING LIGHT SOURCE AGING

(75) Inventors: Oleg Gonopolskiy, West Bloomfield, MI (US); Arik Anderson, Birmingham, MI (US); Bruce J. Barrett, Birmingham, MI (US); Ronald A. Widman, Macomb, MI (US)

(73) Assignee: Covidien LP, Mansfield, MA (US)

( * ) Notice: Subject to any disclaimer, the term of this patent is extended or adjusted under 35 U.S.C. 154(b) by 822 days.

(21) Appl. No.: 12/330,799

(22) Filed: Dec. 9, 2008

(65) Prior Publication Data

US 2010/0145645 A1   Jun. 10, 2010

(51) Int. Cl.
*G01R 19/00* (2006.01)
*G01R 31/26* (2014.01)
*A61B 5/1455* (2006.01)
*H05B 37/03* (2006.01)

(52) U.S. Cl.
CPC ........ *G01R 31/2635* (2013.01); *A61B 5/14553* (2013.01); *H05B 37/03* (2013.01); *A61B 2560/0223* (2013.01)

(58) Field of Classification Search
CPC .............. G01R 31/2635; G01R 19/00; A61B 5/14553; A61B 2560/0223; H05B 37/03
USPC ........ 702/34, 57, 64; 700/175, 176, 286–298; 250/200, 206
See application file for complete search history.

(56) References Cited

U.S. PATENT DOCUMENTS

| | | | |
|---|---|---|---|
| 4,773,422 A * | 9/1988 | Isaacson et al. | 600/326 |
| 4,863,265 A * | 9/1989 | Flower et al. | 356/41 |
| 4,942,877 A * | 7/1990 | Sakai et al. | 600/323 |
| 5,259,381 A | 11/1993 | Cheung et al. | |
| 5,477,853 A | 12/1995 | Farkas et al. | |
| 5,859,658 A * | 1/1999 | Hammond | 347/238 |
| 5,917,183 A * | 6/1999 | Sperling | 250/238 |
| 6,553,241 B2 | 4/2003 | Mannheimer et al. | |
| 6,591,123 B2 | 7/2003 | Fein et al. | |
| 6,963,767 B2 | 11/2005 | Rantala et al. | |
| 7,215,985 B2 | 5/2007 | Petersen et al. | |
| 2004/0030231 A1* | 2/2004 | Norris | 600/323 |
| 2005/0187450 A1* | 8/2005 | Chew et al. | 600/323 |
| 2006/0167351 A1 | 7/2006 | Isaacson et al. | |
| 2006/0192748 A1* | 8/2006 | Lowles et al. | 345/102 |
| 2007/0166047 A1* | 7/2007 | Berger et al. | 398/155 |
| 2008/0116818 A1* | 5/2008 | Shteynberg et al. | 315/192 |
| 2009/0326595 A1* | 12/2009 | Brockway et al. | 607/3 |

FOREIGN PATENT DOCUMENTS

WO      WO 2005079121 A2 *   8/2005

* cited by examiner

*Primary Examiner* — Patrick Assouad
*Assistant Examiner* — Haidong Zhang
(74) *Attorney, Agent, or Firm* — Harness, Dickey & Pierce, PLC

(57) ABSTRACT

A physiological sensor includes a light source and an age detector circuit in communication with the light source. The age detector circuit is configured to determine an age of the light source based on current-voltage characteristics of said light source. In addition, a method includes measuring an initial I-V characteristic and an actual I-V characteristic of the light source, and comparing the initial I-V characteristic to the actual I-V characteristic since changes in the I-V characteristics indicate aging. Actual I-V characteristics can be compared between light sources when they age at different rates to determine light source aging. Moreover, the method may include updating the memory device with the actual I-V characteristic at predetermined times.

17 Claims, 2 Drawing Sheets

SYSTEM AND METHOD OF DETERMINING LIGHT SOURCE AGING

BACKGROUND

Physiological sensors such as pulse and cerebral oximeters use light to measure a variety of physiological characteristics in body tissue. The physiological sensor generally includes a sensor pad assembly with a plurality of light sources in optical communication with at least one light detector. When activated, the light sources transmit light at specific wavelengths through the body tissues to the light detector. The amount of light received by the light detector after attenuation by the body tissue is indicative of the physiological characteristic being tested.

As the light source ages, the output of light by the light source decreases. For example, the output by the light source may decrease by 15% after only 100 hours of operation. In some cases, the decrease in output is not significant. For example, pulse oximeters generally do not depend on light source intensity so long as the intensity is high enough to maintain high signal to noise ratios. However, cerebral oximeters are often affected by light source aging because they employ multiple light sources and at least two light detectors to generate an absorption profile of the brain, which is at least in part based upon multiple weighted differences of the optical densities at different wavelengths from different detector locations.

Until now, light source aging was not a problem for cerebral oximetry because cerebral oximeters were only used in operating rooms for approximately 4-8 hours before being discarded or replaced. Light source aging for such a short period of operation is negligible. Today, however, cerebral oximeters may operate for several days in, for instance, an intensive care unit (ICU). Because individual light sources on the sensor have different aging characteristics, light source aging during long-term monitoring can cause erroneous readings of the cerebral saturation if appropriate corrective measures are not taken. Therefore, it is useful to know the age of the light source to determine if the readings are accurate. Accordingly, a monitoring system employing a method of determining light source aging is needed.

DETAILED DESCRIPTION

A monitoring system executing a method of determining light source aging includes a light source in communication with an age detector circuit that is configured to detect current-voltage (I-V) characteristics of the light source to indicate aging. In one approach, the age detection circuit uploads the I-V characteristics to a memory device, and the monitoring system may also include an interference detection circuit that measures interference caused by external electromagnetic energy sources and only allows the memory device to be updated when substantially no interference is present. Accordingly, the method includes measuring an initial I-V characteristic and an actual I-V characteristic of the light source, and comparing the initial I-V characteristic to the actual I-V characteristic since changes in the I-V characteristics indicate aging. Moreover, the method may include updating the memory device with the actual I-V characteristic at predetermined times to reduce interference.

Figure 1:
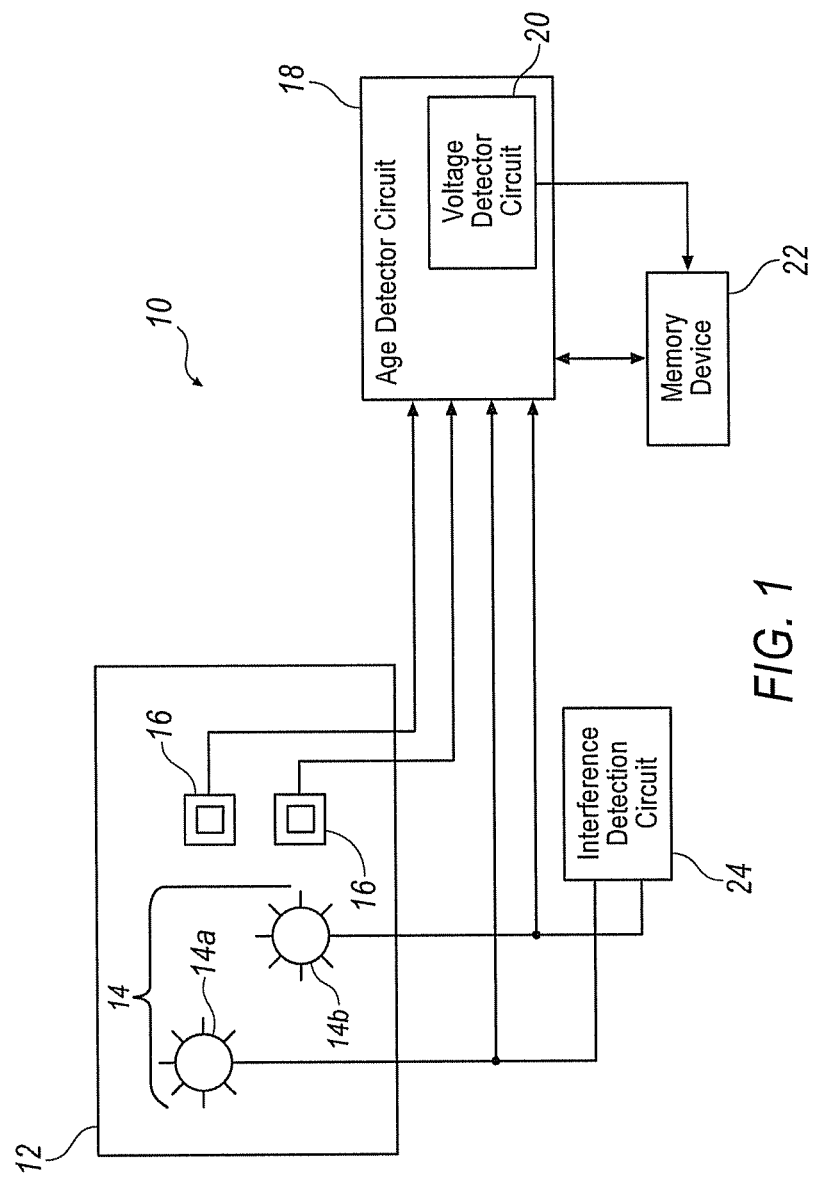
FIG. 1 is a schematic diagram of an exemplary monitoring system.

Referring to FIG. 1, an exemplary monitoring system includes a physiological sensor 10 that has at least one sensor pad 12 having one or more light sources 14 in optical communication with one or more light detectors 16. The exemplary physiological sensor 10 of FIG. 1 illustrates two light sources 14 and two light detectors 16 disposed on a single sensor pad 12, although the light sources 14 and light detectors 16 may be disposed on multiple or different sensor pads 12. The physiological sensor 10 further includes an age detector circuit 18 configured to determine an age of the light sources 14 based on I-V characteristics of the light sources 14. As discussed in greater detail below, one way to determine the I-V characteristics is to measure a forward voltage of the light sources 14 with a voltage detector circuit 20. The age detector circuit 18 may use the I-V characteristics to determine or track the total amount of time any of the light sources 14 has been illuminated. In particular, the age detector circuit 18 may compare an initial I-V characteristic of each of the light sources 14 to an actual I-V characteristic of the light sources 14 measured, the difference of which indicates the age of the light sources 14.

The physiological sensor 10 further includes a memory device 22 capable of storing information in a tangible computer readable medium, and specifically, the initial and actual I-V characteristics of the light sources 14. The memory device 22 may be any type of non-volatile computer memory, such as electrically erasable programmable read only memory (EEPROM). The memory device 22 may be part of the age detector circuit 18, or as illustrated, merely in communication with the age detector circuit 18. In either configuration, the age detector circuit 18 updates the memory device 22 with the actual I-V characteristics, and accesses the memory device 22 to determine the initial I-V characteristic. However, the age detector circuit 18 may only update the memory device 22 at predetermined times to reduce corruption by the light sources 14 or external sources, including RF sources. Specifically, the memory device 22 is susceptible to corruption by external RF sources, such as electro-surgery equipment, especially during a write cycle. Moreover, writing information to the memory device 22 interferes with the ability of the physiological sensor 10 to measure light. To prevent such interference, the physiological sensor 10 may include an interference detection circuit 24 in communication with the memory device 22 and the age detector circuit 18. The interference detection circuit 24 measures interference caused by external RF sources, and allows the age detector circuit 18 to communicate with the memory device 22 based on the interference measured, such as, for example, when substantially no RF interference is measured. Furthermore, communication with the memory device 22 may generate interference with the measurement of light so communication may be limited to times when substantially no light measurements are taking place.

To get the initial I-V characteristic, the age detector circuit 18 must be calibrated. During calibration, light outputs from light sources 14, along with the forward voltage of the light sources 14, are stored in and may be retrieved from the memory device 22. In order to meet an accuracy goal, the relative change of the light output of the light sources 14 during operation should be very low—for example, less than 1.0%, and preferably, less than 0.5%. At the same time, light output from each individual light source 14 should be maintained within 5%.

It will now be explained how forward voltage may be used to determine the age of the light sources 14. The forward voltage ($V_f$) of the light sources 14 can be described using the following equation:

$$V_f = (nkT/q)\mathrm{Ln}(1 + I_f/I_0). \tag{1}$$

In Equation (1), $I_f$ is the current, $I_0$ is the diode saturation current, 'q' is the electron charge, $V_f$ is the forward voltage, T is the junction temperature, 'k' is Boltzmann's constant, and 'n' is the radiative constant that is related to the recombination rate of each light source 14. The radiative constant 'n' is equal to 1 for normal radiative recombination and equal to 2 for non-radiative recombination. While 'n' varies among light sources 14, it increases as the light source 14 ages.

During long term monitoring, the temperature T and radiative constant 'n' are both changing. The radiative constant 'n' changes due to aging, and the temperature may change because the physiological sensor 10 is applied to a patient's body, which may be cooled during surgery. However, in Equation (1), T and 'n' are multiplied together, so changes in the forward voltage due to aging and temperature become indistinguishable. Therefore, the following equation may be used to separate the effects that temperature has on aging:

$$T - T_0 \approx T_a - T_{a0}. \tag{2}$$

In Equation (2), $T_0$ and $T_{a0}$ are the junction temperature and the ambient temperature during calibration, respectively, and $T_a$ is the current ambient temperature. Equation (2) states that changes in the temperatures of the light sources 14 are proportional, if not equal, to changes in the ambient temperature.

According to Equations (1) and (2), the initial forward voltage stored in the memory device 22 may be adjusted to compensate for the current ambient temperature. This way, the only remaining variable concerning aging of the light sources 14 is the radiative constant 'n.' With temperature no longer a factor, the difference between the initial/adjusted forward voltage and the measured forward voltage is due to aging. It is to be appreciated that changes in the ambient temperature can be measured using the light detector 16 located on the sensor pad 12, and specifically, by monitoring the forward voltage of the light detector 16.

To determine aging of multiple light sources 14, one of the light sources 14 may serve as a reference for one or more other light sources 14. In particular, the rate of change of the radiative constant 'n' depends on the wavelength of each of the light sources 14. For instance, the radiative constant for a first light source 14A having a wavelength of 810 nm is less than for a second light source 14B having a wavelength of 730 nm. However, the first light source 14A may be used as a reference to estimate changes in the forward voltage of the second light source 14B caused by changes in the ambient temperature, in which case, the difference between the estimated initial/adjusted forward voltage and the measured forward voltage of the second light source 14B indicates aging.

The relative change of the forward voltages for the first and second light sources 14 can be written as:

$$\delta V_{f(810)}/V_{f0(810)} = \delta n_{810}/n_{0(810)} + \delta T_{810}/T_{0(810)} \tag{3}$$

$$\delta V_{f(730)}/V_{f0(730)} = \delta n_{730}/n_{0(730)} + \delta T_{730}/T_{0(730)}. \tag{4}$$

In Equations (3) and (4), $V_{f0(810)}$, $V_{f0(730)}$, $n_{0(810)}$, $n_{0(730)}$, $T_{0(810)}$, and $T_{0(730)}$ are the values of the forward voltages, radiative constants, and junction temperatures for the first and second light sources 14 during calibration. The first and second light sources 14 may be mounted on the same frame, and changes in the junction temperatures $\delta T_{810}$ and $\delta T_{730}$ due to changes in the ambient temperature Ta are approximately the same (i.e., $\delta T_{810} \approx \delta T_{730}$). Thus, ignoring $\delta n_{810}$, which is approximately equal to 0 since the first light source 14A is used as a reference, Equation (5) can be derived from Equations (3) and (4):

$$\delta n_{730}/n_{0(730)} = \delta V_{f(730)}/V_{f0(730)} - \delta V_{f(810)}/V_{f0(810)}. \tag{5}$$

Using Equation 5, the age of the light source 14 can be estimated without the effect of the ambient temperature by estimating the changes of the relative difference between the forward voltages of the first and second light sources 14.

Equation (5) merely removes the effect of the ambient and/or junction temperature; it does not account for the temperature dependence of the diode saturation current. To do so, the forward voltages of the first and second light sources 14 must be measured using different currents. Using two different currents results in the following equation that is similar to Equation (1):

$$\Delta V_f = (nkT/q)\mathrm{Ln}(I_1/I_2). \tag{6}$$

In Equation (6), $\Delta V_f$ is equal to the difference between the forward voltages of the first and second light sources 14. Accordingly, Equation (5) can be rewritten as Equation (7), below:

$$\delta n_{730}/n_{0(730)} = \delta \Delta V_{f(730)}/\Delta V_{f0(730)} - \delta \Delta V_{f(810)}/\Delta V_{f0(810)}. \tag{7}$$

Equation (7) provides an accurate prediction of the aging of the light sources 14, but also indicates that the forward voltages and excitation currents of the first and second light sources 14 must be continuously monitored and then stored in the memory device 22.

Equations (6) and (7) assume that the currents $I_1$ and $I_2$ are small, for example, less than 100 uA, and the voltage across each light source 14 drops due to resistance in the first and second light sources 14 and/or wiring in the physiological sensor 10. Typically, this voltage drop is much less than the forward voltages of the first and second light sources 14. For example, the voltage drop is typically much less than 1.5 to 2 volts. However, if this is not the case, the following equation may be used to compensate for voltage drops caused by resistance in the light sources 14 or from the wiring of the physiological sensor 10:

$$V_f = (nkT/q)\mathrm{Ln}(1 + I/I_0) + (R_F * I). \tag{8}$$

In Equation (8), $R_F$ is additional resistance caused by a cable, connectors, and circuit board, and I is the current contributing to the forward voltage measurement. The value of (nkT/q) can be found if three values of the forward voltage probing currents $I_1$, $I_2$, and $I_3$ are used, as shown below in Equation (9):

$$(nkT/q) = (I_3(V_2 - V_1) - I_2(V_3 - V_1) + I_1(V_3 - V_2))/(I_3 * \ln(I_2/I_1) - I_2 * \ln(I_3/I_1) + I_1 * \ln(I_3/I_2)). \tag{9}$$

From Equation (9), nkT/q can be calculated as a linear superposition $V_s$ of the three forward voltages $V_1$, $V_2$, and $V_3$, corresponding to the probing currents $I_1$, $I_2$, and $I_3$. In other words, $(nkT/q) = V_s$, where $$V_s = aV_1 + bV_2 + cV_3. \tag{10}$$

The coefficients a, b, and c correspond to various probing current levels. Accordingly, similar to Equation (5), $$\delta n_{730}/n_{0(730)} = \delta V_{s(730)}/V_{s0(730)} - \delta V_{s(810)}/V_{s0(810)}. \tag{11}$$

Using Equations (1)-(11), it is appreciated that spectrometric measurements are sensitive to the differences in the output of the light source 14. Large negative differences between $\delta \Delta V_{f(730)}/\Delta V_{f0(730)}$ and $\delta \Delta V_{f(810)}/\Delta V_{f0(810)}$ from Equation (7) may be attributed to aging, and the light source 14 should be treated as expired if such a large negative difference exists.

Figure 2:
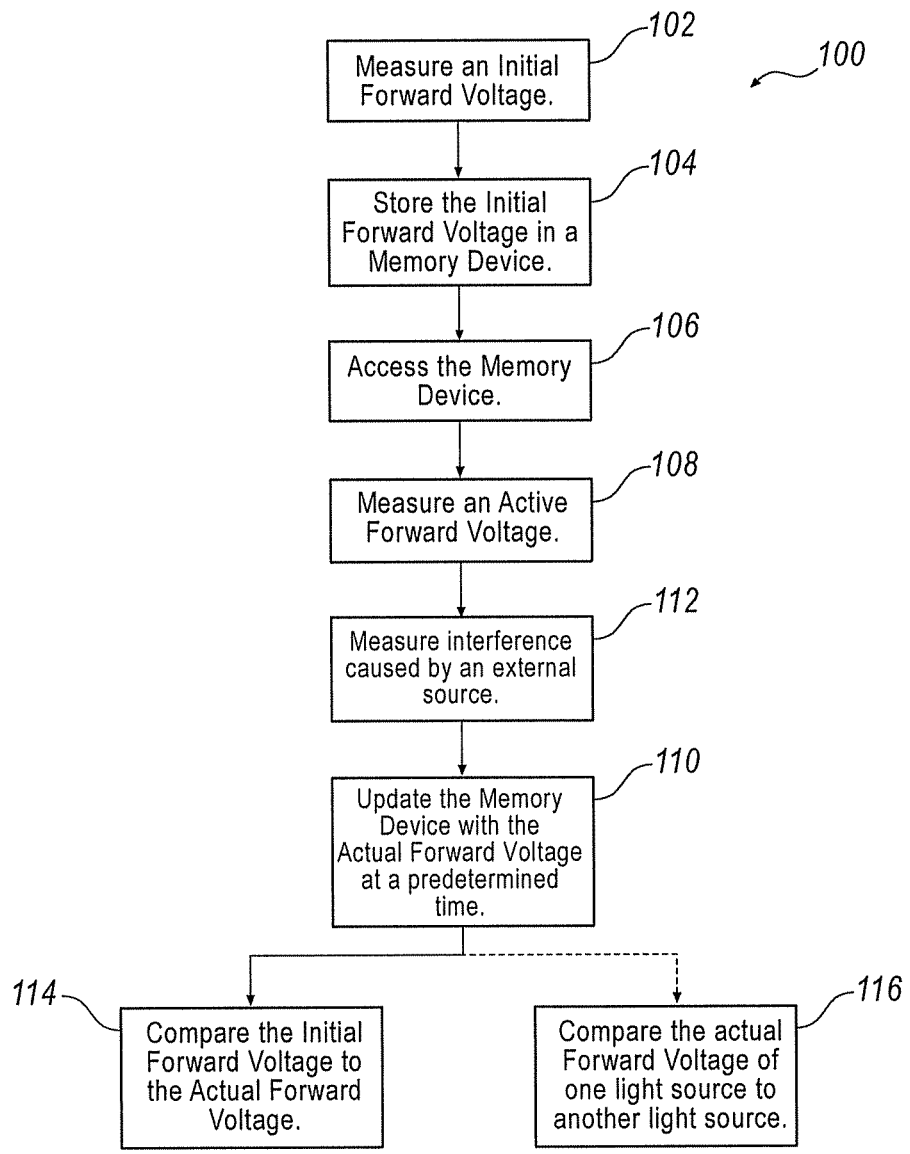
FIG. 2 is a flowchart of an exemplary method of determining light source aging.

FIG. 2 is a flowchart illustrating an exemplary method 100 of determining the age of the light source 14 as previously described. The method 100 generally includes measuring the initial I-V characteristic of the light source 14, measuring the actual I-V characteristic of the light source 14, and comparing the initial I-V characteristic of the light source 14 to the actual I-V characteristic of the light source 14.

The difference between the initial I-V characteristic and the actual I-V characteristic, and specifically the initial forward voltage and the actual forward voltage measured, indicates the age of the light source 14. Therefore, in one exemplary approach, measuring the initial I-V characteristic may include a step 102 of measuring an initial forward voltage of the light source 14. To determine the initial I-V characteristics, including the initial forward voltage, the method 100 may include calibrating the physiological sensor 10 as previously described. Once known, the method 100 may include a step 104 of storing the initial I-V characteristic of the light source 14 in the memory device 22, and accordingly, a step 106 of accessing the memory device 22 to retrieve the initial I-V characteristic of the light source 14.

Likewise, measuring the actual I-V characteristic of the light source 14 may include a step 108 of measuring an actual forward voltage of the light source 14 while the light source 14 is operating (i.e., emitting light). The actual I-V characteristics are updated to the memory device 22, however, to reduce interference, the method 100 may further include a step 110 of updating the memory device 22 with the actual forward voltage, or other I-V characteristic, at a predetermined time. To determine when the memory device 22 should be updated, the method 100 may include a step 112 of measuring interference caused by an external source or the light source 14 and updating the memory device 22 when substantially no interference is measured, when substantially no RF interference is measured, when substantially no light is emitted from the light source 14, and/or when no forward voltage is passing through the light source 14. Moreover, the method 100 may include changing the polarity of the clock signal of the memory device 22 when substantially no light is measured from the light source 14.

Once the initial and actual I-V characteristics are stored in the memory device 22, the age of the light source 14 may be determined by comparing the initial I-V characteristic to the actual I-V characteristic of the light source 14. Specifically, the method 100 may include a step 114 of comparing the initial forward voltage to the actual forward voltage of the light source 14 using Equations (1)-(11). Alternatively, the method 100 may include a step 116 of comparing the actual forward voltage of one light source 14 with the actual forward voltage of another light source 14 to determine light source aging.

It is to be understood that the above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

We claim:

1. A monitoring system comprising:
a sensor having a light source; and
an age detector circuit in communication with said light source and configured to determine an age of said light source based on a current-voltage characteristic of said light source;
wherein said age detector circuit includes a memory device configured to store an initial current-voltage characteristic of said light source and wherein said age detector circuit is configured to update said memory device with an actual current-voltage characteristic of said light source that is measured after storing the initial current-voltage characteristic of said light source; and
an interference detection circuit in communication with said memory device and said age detector circuit and wherein the interference detection circuit is configured to measure interference caused by an external source of electromagnetic energy and allow said age detector circuit to communicate with said memory device only when no substantial interference from a source of electromagnetic energy is present.

2. A monitoring system as set forth in claim 1, wherein said age detector circuit is configured to compare the initial current-voltage characteristic of said light source to the actual current-voltage characteristic of said light source to determine the age of said light source.

3. A monitoring system as set forth in claim 1, wherein said interference detection circuit is configured to allow said age detector circuit to communicate with said memory device when substantially no light is emitted from said light source.

4. A monitoring system as set forth in claim 2, wherein said age detector circuit includes a voltage detector circuit in communication with said light source and wherein said voltage detector circuit is configured to measure the actual current-voltage characteristics of said light source.

5. A monitoring system as set forth in claim 4, wherein said voltage detector circuit is configured to detect a forward voltage of said light source.

6. A monitoring system as set forth in claim 1, wherein said initial current-voltage characteristic and said actual current-voltage characteristic each comprises a forward voltage of the light source.

7. A method comprising:
measuring an initial current-voltage characteristic of a light source of a physiological sensor;

storing the initial current-voltage characteristic in a memory device;

measuring an actual current-voltage characteristic of the light source;

measuring interference caused by an external source of electromagnetic energy;

updating the memory device with the actual current-voltage characteristic of said light source that is measured after to storing the initial current-voltage characteristic of said light source, wherein the updating of the memory is allowed to occur only while no substantial interference from a source of electromagnetic energy is present; and comparing the initial current-voltage characteristic of the light source to the actual current-voltage characteristic of the light source to determine an age of the light source.

8. A method as set forth in claim 7, further comprising accessing the memory device to retrieve the initial current-voltage characteristic of the light source.

9. A method as set forth in claim 7, further comprising updating the memory device when substantially no light is emitted from said light source.

10. A method as set forth in claim 7, further comprising updating the memory device when no forward voltage passing through the light source is measured.

11. A method as set forth in claim 7, wherein measuring the initial current-voltage characteristic of the light source includes measuring an initial forward voltage of the light source.

12. A method as set forth in claim 11, wherein measuring the actual current-voltage characteristic of the light source includes measuring an actual forward voltage of the light source.

13. A method as set forth in claim 12, wherein comparing the initial current-voltage characteristic of the light source to the actual current-voltage characteristic of the light source includes comparing the initial forward voltage of the light source to the actual forward voltage of the light source to determine the age of the light source.

14. A monitoring system as set forth in claim 7, wherein said initial current-voltage characteristic and said actual current-voltage characteristic each comprises a forward voltage of the light source.

15. A monitoring system comprising:

a physiological sensor having a light source; and an age detector circuit in communication with said light source and configured to determine an age of said light source based on a current-voltage characteristic of said light source;

wherein said age detector circuit includes a memory device configured to store an initial current-voltage characteristic of said light source and wherein said age detector circuit is configured to update said memory device with an actual current-voltage characteristic; and an interference detection circuit in communication with said memory device and said age detector circuit and wherein the interference detection circuit is configured to measure interference caused by an external source of electromagnetic energy and allow said age detector circuit to communicate with said memory device only when no substantial interference from a source of electromagnetic energy is present;

wherein said age detector circuit is configured to adjust the initial current-voltage characteristic stored in the memory device to compensate for a current ambient temperature.

16. A monitoring system as set forth in claim 15, wherein the initial current-voltage characteristic stored in the memory device is an initial forward voltage of the light source.

17. A monitoring system as set forth in claim 15, wherein said initial current-voltage characteristic and said actual current-voltage characteristic each comprises a forward voltage of the light source.

* * * * *